United States Patent [19]
Tolkoff et al.

[11] Patent Number: 5,857,585
[45] Date of Patent: Jan. 12, 1999

[54] LIGATING BAND DISPENSER

[75] Inventors: M. Joshua Tolkoff, Brookline; Fernando Alvarez de Toledo, Concord; Andrew Ziegler, Arlington; Wayne A. Minter, Peabody, all of Mass.

[73] Assignee: Act Medical, Inc., Waltham, Mass.

[21] Appl. No.: 654,374

[22] Filed: May 28, 1996

[51] Int. Cl.⁶ .................................................. B65H 3/00
[52] U.S. Cl. ..................... 221/36; 221/312 R; 606/140
[58] Field of Search .................... 606/140, 141, 606/135, 165; 221/36, 40, 41, 312 C, 312 R

[56] References Cited

U.S. PATENT DOCUMENTS

5,398,844   3/1995   Zaslavsky et al. ...................... 606/140
5,624,453   4/1997   Ahmed .................................... 606/140

Primary Examiner—William E. Terrell
Assistant Examiner—Khoi H. Tran
Attorney, Agent, or Firm—Kenyon & Kenyon

[57] ABSTRACT

A ligating band dispenser for attachment to the distal end of a ligating device having proximal and distal ends with a lumen extending therebetween and being adapted for supporting a plurality of ligating bands includes a support for attachment to the distal end of the ligating device and for carrying the plurality of ligating bands and having a passage communicating with the lumen; and a dispenser including a first displacement element looped about each of the bands in series attached to the support and extending through the passage and lumen whereby proximal motion of the operator element from the proximal end of the ligating device transfers individually the most distal ligating band off the distal end of the support.

10 Claims, 7 Drawing Sheets

LIGATING BAND DISPENSER

FIELD OF INVENTION

This invention relates to a ligating band dispenser for attachment to the distal end of an endoscopic device having proximal and distal ends with a lumen extending therebetween and being adapted for supporting a plurality of ligating bands, and more particularly to such a dispenser which employs a single displacement element to dispense a plurality of bands sequentially and individually.

BACKGROUND OF INVENTION

It is well known that one can treat various types of lesions including hemorrhoids and esophageal varices by ligation. The object of ligation is to position an elastic cord, or ligating band, around the lesion to stop circulation through the tissue and allow the tissue to die whereupon the body sloughs off the dead tissue. One instrument for facilitating the placement of a single ligating band or set of bands includes, at its distal end, a ligating band dispenser comprising two rigid, concentric tubes. The tubes can slide with respect to each other under the control of a trigger mechanism at the proximal end of the instrument. A rigid endoscope having internal passages forming a suction path and a light path interconnect the trigger mechanism and dispenser. The dispenser inner tube can be loaded with a set of one or more elastic rings or ligating bands. A separate stopper bar attaches to the instrument to prevent premature dispensing. When the instrument is located proximate a lesion, a surgeon removes the stopper bar and applies suction to draw tissue into the hollow passage at the distal end of the dispenser. Pulling on the trigger retracts the inner tube. The larger diameter of the outer tube engages the ligating band so the band cannot displace with the inner tube. As the inner tube is withdrawn from the ligating band, it slides off the inner tube and elastically contracts onto the tissue.

Another instrument includes a ligating band dispenser with an inner tube that moves with respect to an outer tube to dispense a ligating band. This dispenser is oriented at right angles to the rigid endoscope and includes a structure for moving the inner tube of the dispenser in this configuration.

A third similar dispenser approach includes an inner tube that moves axially with respect to an outer tube at the distal end of the instrument. The outer tube attaches axially onto the distal end of the endoscope. An operating mechanism in the form of a pull wire with a weighted handle maintains tension on the inner tube so that it does not displace axially outwardly while the instrument is being positioned. For some applications it is suggested that the endoscope structure be inserted through an overtube to prevent premature dispensing. Suction can be applied to draw tissue into the central aperture of the dispenser formed by the inner tube. Then a surgeon pulls the handle and retracts the inner tube axially past the distal end of the outer tube to force the ligating band of the instrument onto the tissue.

Each of the foregoing instruments dispenses a single ligating band or a single set of ligating bands at a single location. None suggests dispensing ligating bands at discrete locations. These instruments apparently would have to rely on a surgeon's sense of touch in order to displace the inner tube by an incremental distance corresponding to the thickness of a stretched ligating band to deposit a plurality of bands at different sites. That would be very difficult to accomplish.

Indeed, when it was desired to deposit ligating bands at different sites, the common practice was to load and dispense one band and to withdraw the entire instrument from the patient and load a new ligating band onto the inner tube each time. Loading ligating bands onto an instrument requires special tools and can be time consuming, particularly if the special tooling must be available to install each ligating band individually while the instrument is withdrawn. Each of these instruments requires some structure, such as special stoppers or overtubes, for preventing the premature dispensing of the ligating band. Consequently, none of these instruments is readily adaptable for dispensing ligating bands at different sites without withdrawing the instrument after each individual site is ligated.

Another device, a multiple ligating band dispenser for ligating instruments includes interfitted inner and outer structures that support a plurality of ligating bands at axially spaced locations. Retraction of the inner structure dispenses one ligating band. Extension of the inner structure advances the remaining ligating bands distally, axially so the next retraction dispenses another ligating band. This ligating band dispenser overcomes some but not all of the undesirable characteristics of single-band dispensers. For example, prior art single-band dispensers can eject a ligating band inadvertently if, during placement, tissue at the distal end of the dispenser, rather than the physician, moves the distal edge of the movable tube. The multiple band dispenser overcomes this problem by using a spring to bias the movable tube to a distal position. However, the use of the spring increases the force that must be used during the dispensing operation. Also, the distal edge of the movable tube is the most distal part of the dispenser. During placement, this edge engages the lesion to form a vacuum seal thereby allowing the lesion to be withdrawn into the lumen of the endoscope. When the movable tube moves proximally during the dispensing operation, the vacuum seal can break thereby enabling the lesion to pull away from the dispenser.

In one attempt at dispensing a plurality of ligating bands individually and sequentially, a support, coaxially attached to the distal end of an endoscope, carries the plurality of ligating bands at axially spaced positions along an exterior surface. There are two concentric tubes with grooves inside the outer tube. The elastic ligating bands are positioned between the tubes and within the grooves so that rotation of the outer tube by means of a screw mechanism advances all the bands. This allows the bands to be sequentially advanced off the end of the dispenser. In another embodiment there are two concentric tubes, the inner being rigid and the outer being a flexible fabric. The bands are arranged on the outer surface of the fabric tube separated by small protrusions forming grooves on which the bands rest. The distal edge of the fabric is folded over the distal edge of the rigid tube so that it may be pulled proximally inside the rigid tube. A cable is provided to pull the fabric tube inward, causing the bands to be sequentially released from the end of the device. Both advance all the ligating bands simultaneously. Due to the strong elastic force applied by the bands on the housing and the friction between the bands and the housing, moving all bands at the same time requires significant pull force. In addition, moving all the bands simultaneously increases the likelihood of inadvertently firing two or more bands simultaneously.

Another attempt for dispensing a plurality of ligating bands individually and sequentially uses a support, coaxially attached to the distal end of an endoscope, and carries the plurality of ligating bands at axially spaced positions along an exterior surface. One or more displacement filaments are looped around each band; each filament then loops over the distal edge of the dispenser where it is secured. The other end of each filament runs beneath the band, over the distal edge of the dispenser and joins with a pull wire which exits the proximal end of the endoscope. When a physician moves the pull wire a certain distance proximally, the filaments sequentially advance each band off the distal edge of the dispenser, releasing the securing means as the band slides off the distal end of the dispenser. Various means are described to enable a single pull wire to sequentially advance multiple sets of filaments.

This approach overcomes some of the drawbacks of earlier devices. In treating lesions of the esophagus or other difficult to approach structures, it is desirable to have a sufficient number of ligating bands to assure completion of the procedure without the necessity of removal and reinsertion of the endoscope. Although this device can deliver multiple bands, it has some drawbacks. Each band has one or a pair of filaments used for advancing the band over the distal edge of the structure and onto the tissue. A complex attachment harness is used to assure that the series of loops of filaments is displaced sequentially to release only one band at a time from the distal end. Additionally, when the number of bands increases, the assembly labor and manufacturing complexity of assembly of the device becomes significant, and increases considerably with increasing numbers of bands. In addition, the displacement filaments all run though the working channel of the endoscope, and the small diameter of this channel limits the number of filaments. Additionally the filaments may limit the suction and obstruct other functions such as delivery of fluid or other devices through the working channel. The large number of filaments significantly obstructs drawing of tissue into the ligating structure and limits visibility through the end of the device.

SUMMARY OF INVENTION

It is therefore an object of this invention to provide a ligating band dispenser for dispensing plural ligating bands, individually and sequentially at one or many different sites.

It is a further object of this invention to provide such a ligating band dispenser for dispensing plural ligating bands individually without the need to remove the dispenser after each band dispensing.

It is a further object of this invention to provide such a ligating band dispenser which is usable with a variety of ligating devices, endoscopes and similar structures.

It is a further object of this invention to provide such a ligating band dispenser which is reliable, easy to use and reduces the likelihood that the vacuum seal will be broken between the distal end of the dispenser and lesion being treated.

It is a further object of this invention to provide such a ligating band dispenser which reduces to a minimum the number of operator elements necessarily present in the working passage of the dispenser.

It is a further object of this invention to provide such a ligating band dispenser which dispenses plural ligating bands at different locations and allows for passage of other devices, such as sclerotherapy injection needles, through the working channel.

It is a further object of this invention to provide such a ligating band dispenser which dispenses plural ligating bands at different locations, where operation required to dispense the bands does not significantly limit the space or visibility through the working channel which forms the entrance chamber for the tissue drawn into the dispenser in preparation for ligation.

It is a further object of this invention to provide such a ligating band dispenser which is simple to make and use.

It is a further object of this invention to provide such a ligating band dispenser which is particularly useful for esophageal varices.

The invention results from the realization that an improved, simpler ligating band dispenser can be achieved using a single displacement element by looping the element around each band seriatim and attaching it to the band support means so that a single displacement element actuated by a single operation can dispense all of a plurality of ligating bands individually, separately and sequentially.

This invention features a ligating band dispenser for attachment to the distal end of a ligating device having proximal and distal ends with a lumen extending therebetween and being adapted for supporting a plurality of ligating bands. There are support means for attachment to the distal end of the ligating device and for carrying the plurality of ligating bands. The support means has a passage communicating with the lumen of the ligating device. There are dispensing means including a first displacement element looped about each of the bands in series. The displacement element is attached to the support means and extends through the passage and lumen of the ligating device. An operator element extending from the displacement element through the lumen and accessible at the proximal end of the lumen whereby proximal motion of the first displacement element from the proximal end of the ligating device transfers the most distal ligating band off the distal end of the support means.

In a preferred embodiment the support means may include a like plurality of notches and the displacement element may extend through a corresponding notch at least once over, around and under the associated band and return to a notch. For all but the last band the displacement element may extend from the returned to notch to the next notch and then under, around and over the associated band. Dispensing means may include a second displacement element looped about each of the bands in series and spaced about the bands from the first displacement element. The first displacement element may include stop means for arresting movement of the distal end of the displacement element during band dispensing. The support means may include limiter means for preventing withdrawal of the first displacement element from the support means after the last band is dispensed. The dispensing means may include an operator element extending from the displacement element through the lumen of the ligating device and accessible at the proximal end of the lumen. Slack may be provided in at least one of the loops of the displacement element about the bands. The support means may include a distal edge portion and the displacement element may extend distally of the distal edge portion, loop around a corresponding ligating band and releasably attach to the support means at the distal edge portion. The support means may include tubular body means having an exterior cylindrical surface for carrying the ligating bands and having a proximal shoulder portion and may include connector means for connecting the shoulder portion to the proximal end of the ligating device. The dispensing means may include a second displacement element, each displacement being looped about a separate set of at least one band.

DISCLOSURE OF PREFERRED EMBODIMENT

Other objects, features and advantages will occur to those skilled in the art from the following description of a preferred embodiment and the accompanying drawings, in which.

Figure 1:
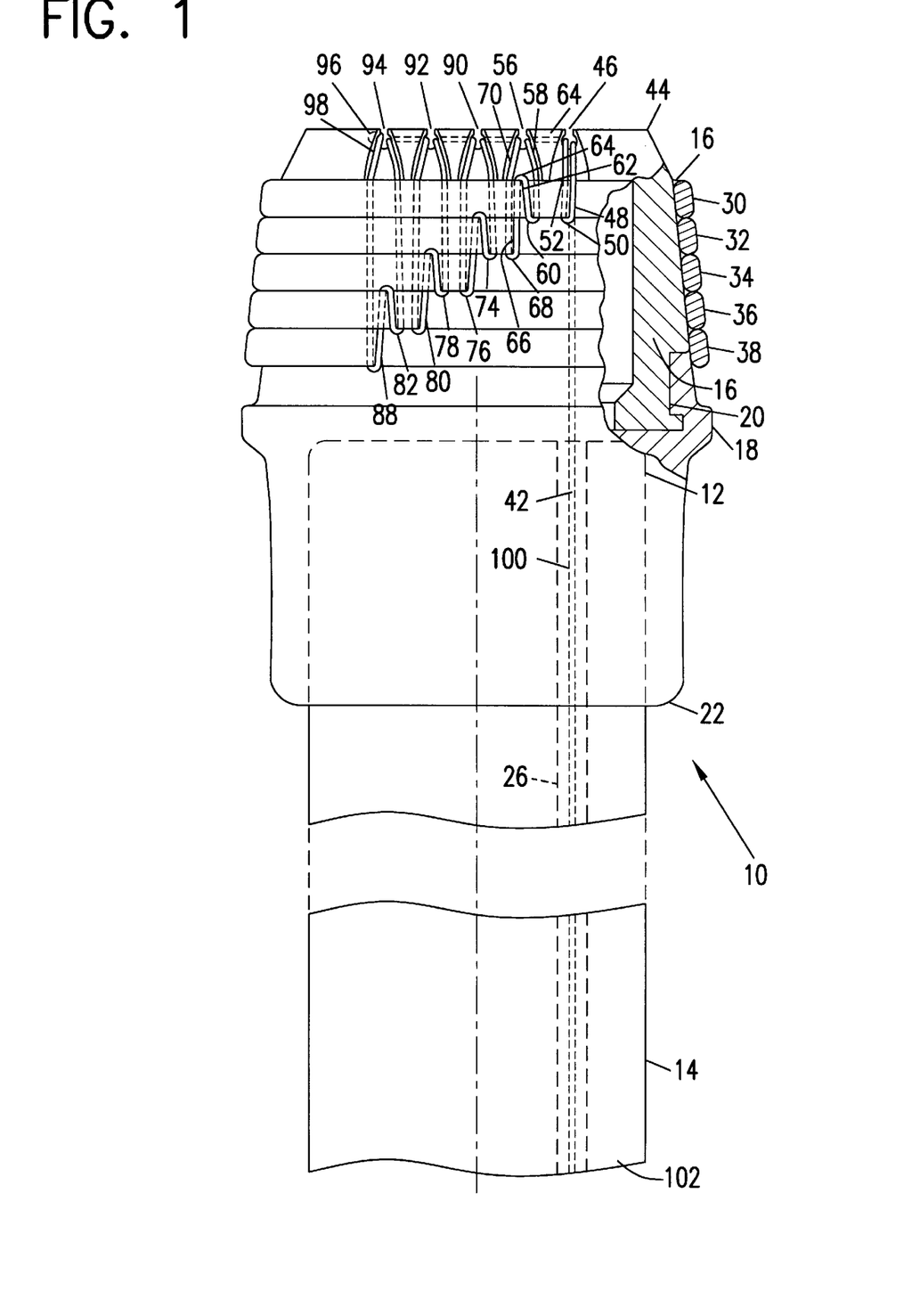
FIG. 1 is a side elevational view with portions broken away of a ligating band dispenser according to this invention mounted on the distal end of a ligating device such as an endoscope showing the special threading pattern of the dispensing element.

There is shown in FIG. 1 a ligating band dispenser 10 according to this invention attached to the distal end 12 of a ligating device such as endoscope 14. Dispenser 10 includes a support 16 which engages flexible connector 18 on shoulder 20. The other portion 22 of connector 18 attaches to the distal end 12 of endoscope 14. Passage 24 in support 16 communicates with lumen 26 in endoscope 14. In accordance with this invention, a plurality of ligating bands 30, 32, 34, 36 and 38 are stretched onto support 16. The entire assembly of ligating band dispenser 10 and endoscope 14 are typically circularly symmetrical about longitudinal axis 40 and are circular in cross section, although this is not a necessary limitation of the invention.

Displacement element 42 extends through passage 24, then lumen 26, and then outwardly over the distal edge 44 of support 16 through notch 46. From there displacement element 42 loops over at 48, around at 50, and under at 52 the first ligating band 30 and then returns to that same notch 46, extends at 54 along the inside edge and exits radially outwardly once again and exits once again through notch 56, whereupon it moves under 58, around 60 and over 62 the first ligating band 30, then under 64 it moves under 58, around 60 and over 62 the first ligating band 30, then under 64 ligating band 30, over 66 the second ligating band 32, around 68 ligating band 32, and under it 70, back to notch 58. The paths of subsequent loops 74, 76, 78, 80, 82 and 88 and their engagement with notches 90, 92 and 94 can be easily traced in FIG. 1. A knot 96 or device of similar function can be placed at the end at 98 of displacement element 42 to prevent it from being pulled through retaining hole 122. Displacement element 42 can be connected to operator element 100 which extends all the way to the proximal end 102 of endoscope 14. Displacement element 42 and operator element 100 may in fact be one and the same thread, filament, wire or string.

Figure 2:
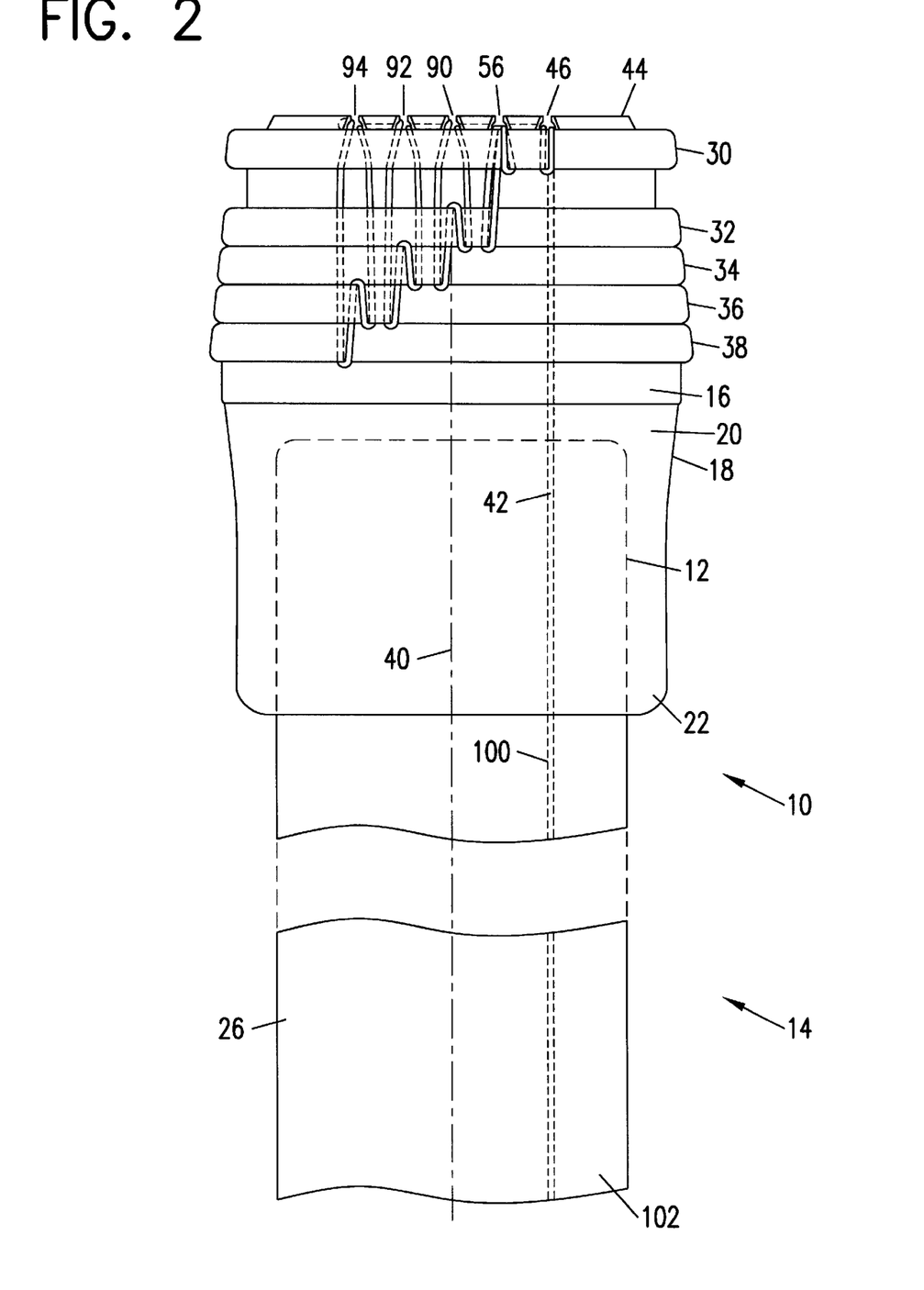
FIG. 2 is a view similar to FIG. 1 with the first ligating band displaced toward the distal end of the dispenser.

As displacement element 42 and/or operator element 100 is pulled to the right in FIG. 2, the first band 30 is moved and/or rolled to the left toward distal end 44 of support 16 of dispenser 10. Continued pulling on element 42 and/or 100 causes band 30 to slide free of distal end 44 of support 16 of dispenser 10. At the moment, depicted in FIG. 3, the loop 110 of the displacement element 42, being free of notches 46 and 56, will unwrap from around band 30, causing the next pull on element 42 to begin movement of the next band 32 to the left. At this time band 30 collapses about the hemorrhoidal tissue which has been vacuum-drawn into the end of support 16 by means of a vacuum supplied through lumen 26 in a conventional fashion.

Figure 3:
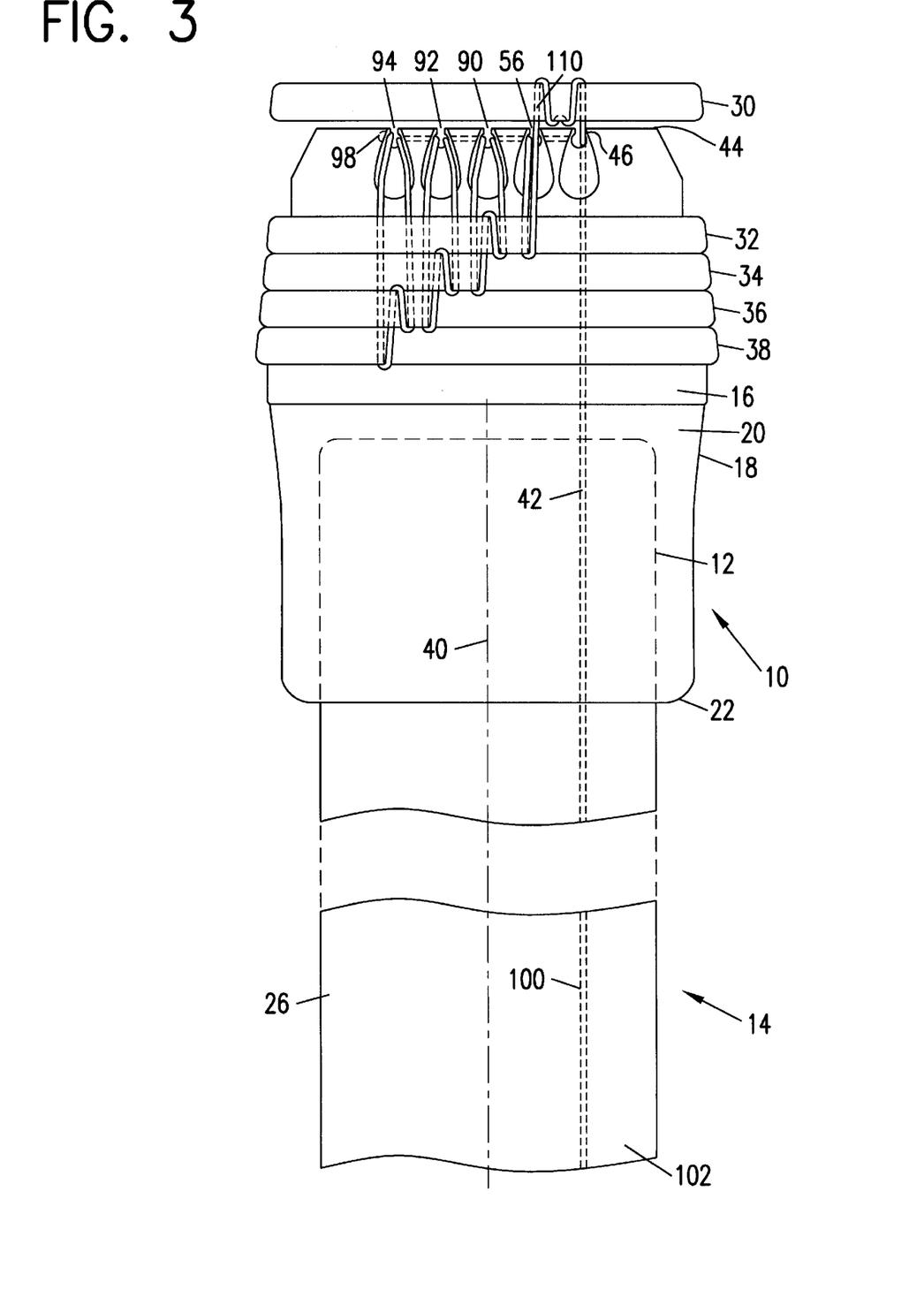
FIG. 3 is a view similar to FIGS. 1 and 2 with the first ligating band clear of the distal edge of the dispenser about to be freed from the displacement element and encircle hemorrhoidal tissue or an esophageal varix.
Figure 4:
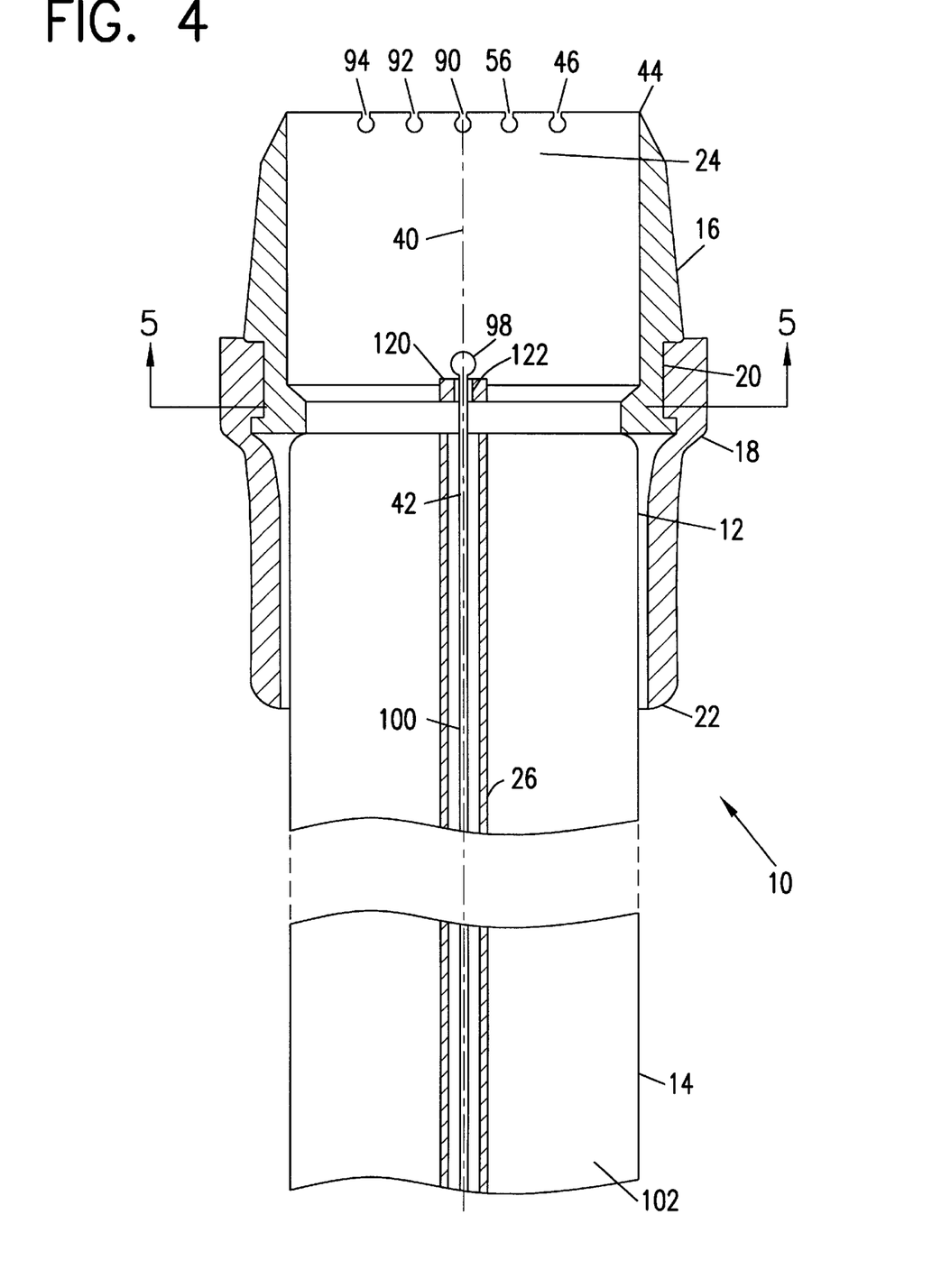
FIG. 4 is a view similar to FIGS. 1–3 showing limiter means for preventing complete withdrawal of the displacement element from the dispenser.
Figure 5:
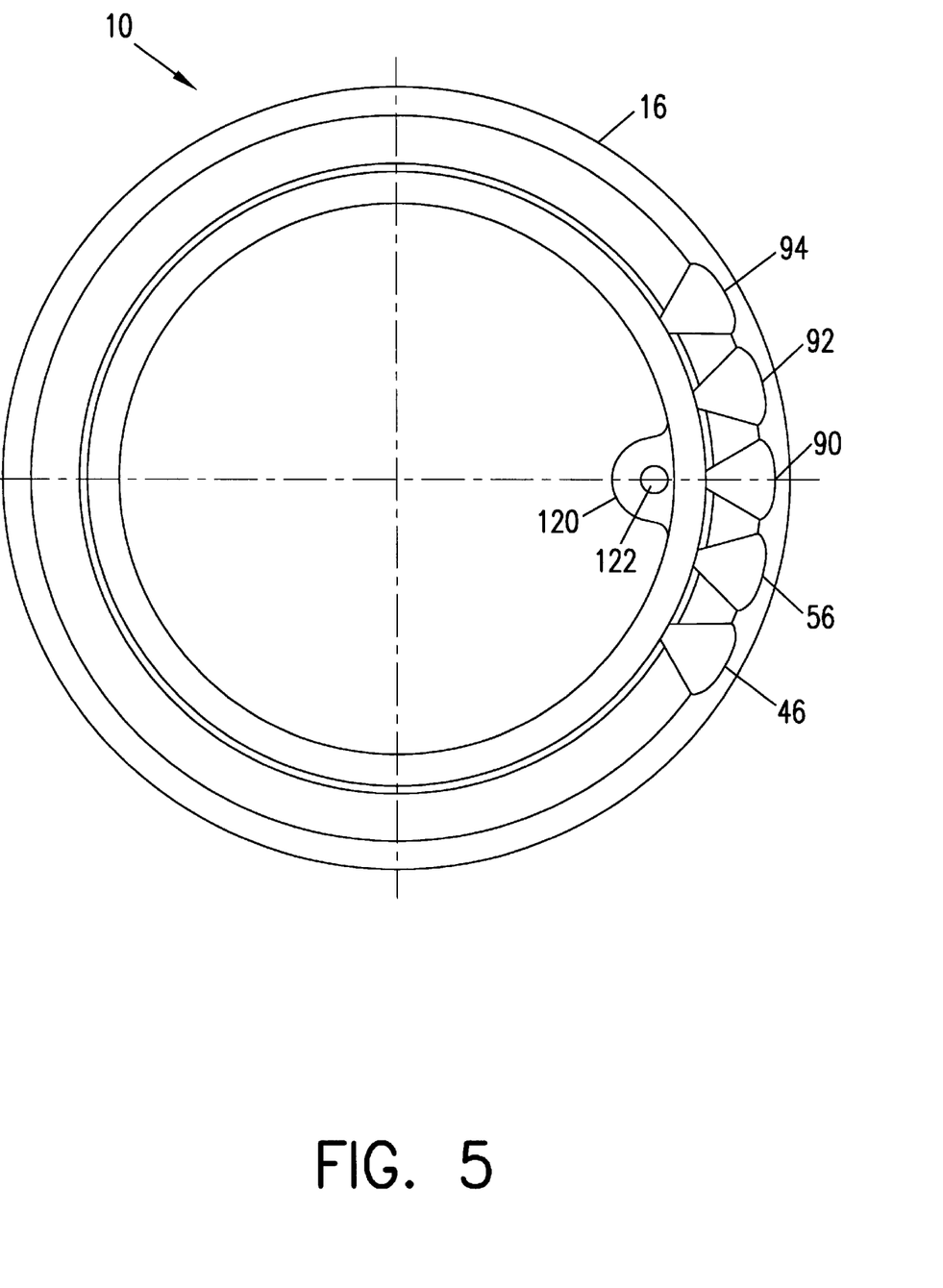
FIG. 5 is a view taken along lines 5—5 of FIG. 4.

The movement of element 42 to the right in FIG. 3 draws up the slack so that further pulling on elements 42 or 100 will begin moving band 32 to the left in the same way as band 30. A limiter 120, FIG. 4, is provided within support 16 to catch the knot 98 or other device of similar function so that even after the last band 38 is dispensed element 42 cannot be completely withdrawn from dispenser 10. This serves to keep dispenser 10 tethered to the distal end 12 of endoscope 14 so that dispenser 10 cannot be inadvertently lost inside the patient. Limiter 120 employs a hole 122 which is smaller than knot 98 so that knot 98 cannot be pulled through it. The structure of limiter 120 and the hole 122 can be seen more clearly in FIG. 5.

Figure 6:
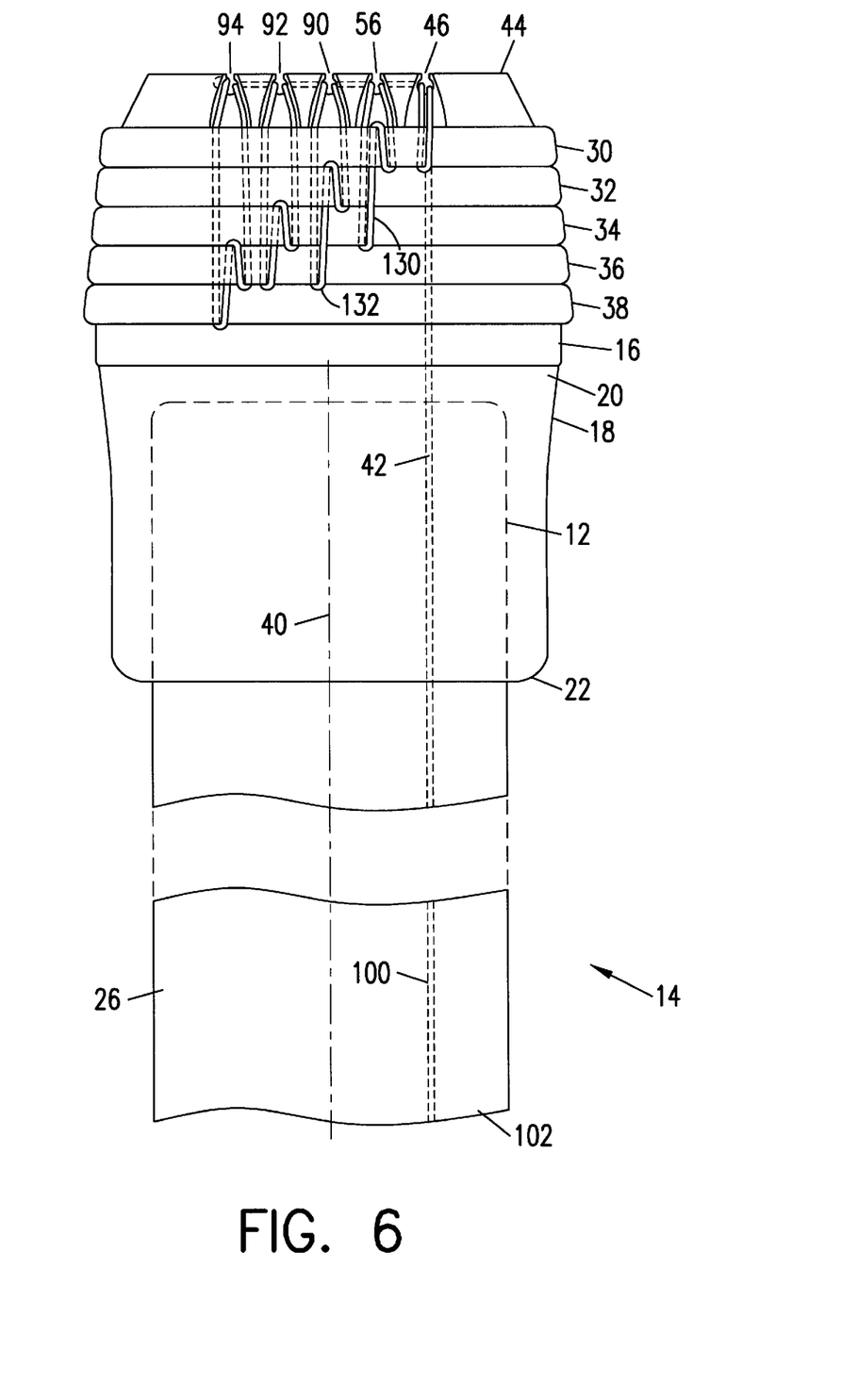
FIG. 6 is a view similar to FIG. 1 showing purposely introduced slack in the loops of the displacement element about some of the ligating bands.

Slack is preferably introduced as slack loops 130, 132, FIG. 6, so that each band 30–38 can be advanced at intervals without moving one or more additional bands simultaneously. This is done for control and to reduce the friction or drag encountered. The movement of two, three or additional bands increases the resistance such that a much stronger force must be applied to element 42 or 100 and such force could pose a danger to the patient or a threat of inadvertent shifting of the dispenser at a critical moment such as when the band is released to encircle the varix or tissue or cause release of multiple bands simultaneously.

The location of each band is progressively further from the distal edge of the dispenser. Therefore, the travel from resting position to release for each successive band increases. The handle at the proximal end of the endoscope for releasing the bands is designed for simplicity for the user so that the handle advances about one inch per band release. It is desirable that the advance for releasing each band be the same so that the user can rely on the uniformity of dispensing. But, since there is a different travel per band, in order to have a uniform advancement, a varying length of slack is used to make up the difference in travel between bands.

The length of string that is woven around the distal band is considerably shorter than that woven around the proximal band. Therefore, if there was no slack in the string between the first and second band, when the string is pulled one inch, two bands would deploy instead of one. Chart I below shows the distance and the slack needed:

CHART I

|        | Length of string woven around band | Length of slack | Total length per band |
|--------|-----------------------------------|-----------------|----------------------|
| Band 1 | .2 inch                           | .8 inch         | 1.0 inch             |
| Band 2 | .4 inch                           | .6 inch         | 1.0 inch             |
| Band 3 | .6 inch                           | .4 inch         | 1.0 inch             |
| Band 4 | .8 inch                           | .2 inch         | 1.0 inch             |
| Band 5 | 1.0 inch                          | 0 inches        | 1.0 inch             |

Chart II shows the slack for eight bands:

CHART II

|        | Length of string woven around band | Length of slack | Total length per band |
|--------|-----------------------------------|-----------------|----------------------|
| Band 1 | .2 inch                           | 1.6 inches      | 1.8 inches           |
| Band 2 | .4 inch                           | 1.4 inches      | 1.8 inch             |
| Band 3 | .6 inch                           | 1.2 inches      | 1.8 inch             |
| Band 4 | .8 inch                           | 1.0 inch        | 1.8 inch             |
| Band 5 | 1.0 inch                          | .6 inch         | 1.8 inch             |

CHART II-continued

|  | Length of string woven around band | Length of slack | Total length per band |
|---|---|---|---|
| Band 6 | 1.2 inches | .4 inch | 1.8 inches |
| Band 7 | 1.4 inches | .2 inch | 1.8 inches |
| Band 8 | 1.6 inches | 0 inches | 1.8 inches |

A length of 1.8 inch of advance per band is not desirable and would be unacceptable to the user. To solve this problem, the eight bands are split into two groups of four. Then the slack would appear as in Chart III:

CHART III

|  | Length of string woven around band | Length of slack | Total length per band |
|---|---|---|---|
| First String |  |  |  |
| Band 1 | .2 inch | .8 inch | 1.0 inch |
| Band 2 | .4 inch | .6 inch | 1.0 inch |
| Band 3 | .6 inch | .4 inch | 1.0 inch |
| Band 4 | .8 inch | .2 inch | 1.0 inch |
| Second String |  |  |  |
| Band 5 | .2 inch | .8 inch | 1.0 inch |
| Band 6 | .4 inch | .6 inch | 1.0 inch |
| Band 7 | .6 inch | .4 inch | 1.0 inch |
| Band 8 | .8 inch | .2 inch | 1.0 inch |

Figure 7:
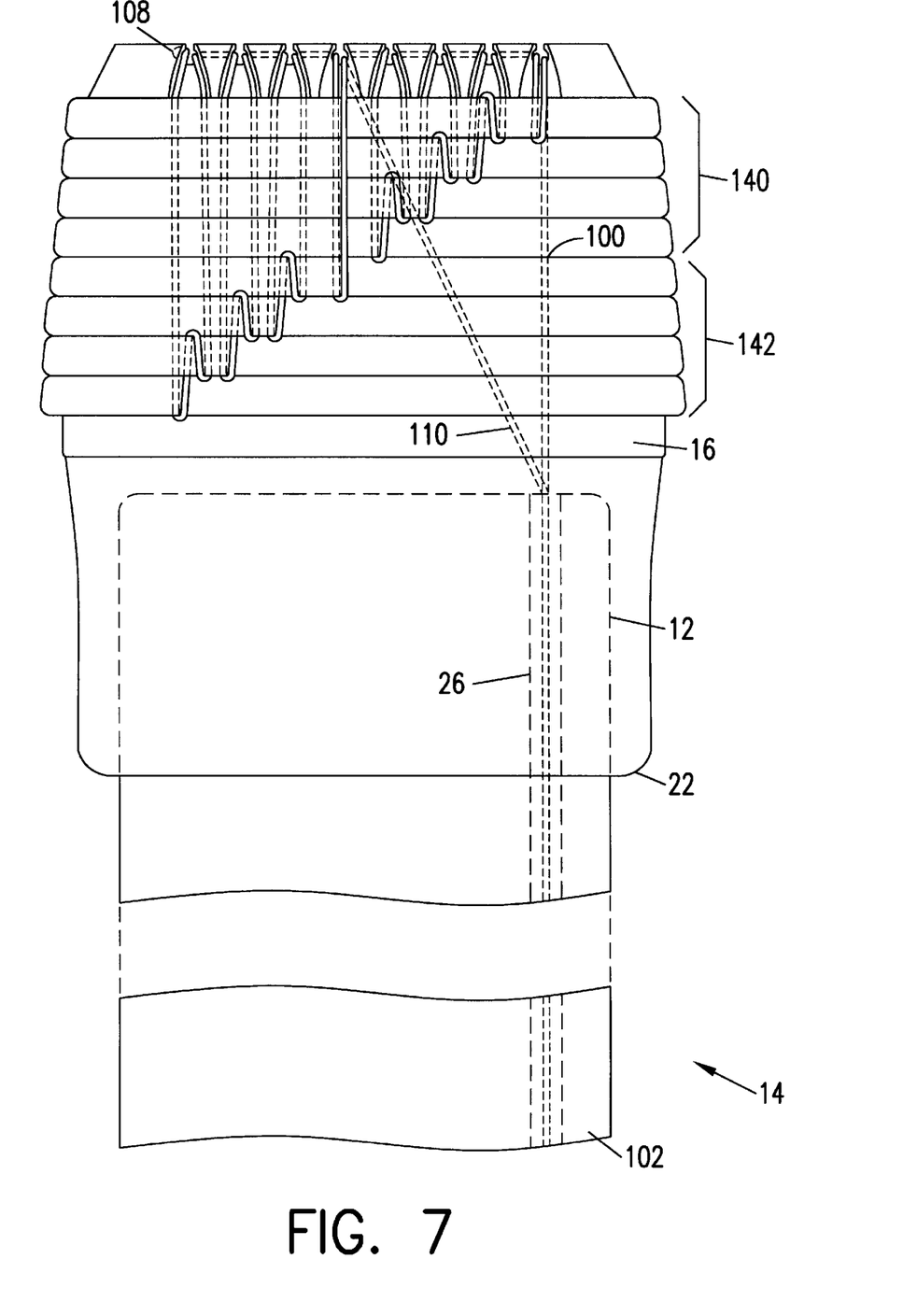
FIG. 7 is a diagrammatic view showing the bands operated in two different groups by two different displacement elements.

The use of two different groups of four bands each is shown in FIG. 7 where support 16 carries two groups of ligating bands, 140 and 142. Displacement element 100 engages the distal series of bands 140. After the bands 140 are deployed, displacement element 110 engages the proximal series of bands 142. After the bands 142 are deployed, the knot 108 lodges into the limiter 120.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A ligating band dispenser for attachment to a distal end of a ligating device, wherein a lumen extends from the distal end of the ligating device to a proximal end thereof and wherein the ligating band dispenser is adapted to support a plurality of first ligating bands, the ligating band dispenser comprising:
   a support structure for attachment to the distal end of the ligating device, wherein the first ligating bands are received around an outer surface of the support structure and wherein a passage extends through the support structure to communicate with the lumen; and
   a first displacement element looped about each of the first ligating bands in series, the first displacement element extending through the passage to a distal end of the lumen, whereby proximal motion of the first displacement element from the proximal end of the ligating device transfers a distal-most one of the first ligating bands off a distal end of the support structure;
   wherein the support structure includes a plurality of notches and, wherein the first displacement element extends through a first one of the notches, over, around and under a first one of the first ligating bands and returns to a returned-to-notch selected from one of the first notch and a corresponding second notch.

2. A ligating band dispenser for attachment to a distal end of a ligating device, wherein a lumen extends from the distal end of the ligating device to a proximal end thereof and wherein the ligating band dispenser is adapted to support a plurality of first ligating bands, the ligating band dispenser comprising:
   a support structure for attachment to the distal end of the ligating device, wherein the first ligating bands are received around an outer surface of the support structure and wherein a passage extends through the support structure to communicate with the lumen; and
   a first displacement element looped about each of the first ligating bands in series, the first displacement element extending through the passage to a distal end of the lumen, whereby proximal motion of the first displacement element from the proximal end of the ligating device transfers a distal-most one of the first ligating bands off a distal end of the support structure;
   wherein the displacement element includes a stop for preventing movement of a distal end of the displacement element proximally past a predetermined position; and
   wherein the support structure includes a limiter which, when the first displacement element has been moved to the predetermined position, contacts the stop to prevent withdrawal of the first displacement element from the support structure after a proximal-most one of the first ligating bands has been dispensed.

3. A ligating band dispenser for attachment to a distal end of a ligating device, wherein a lumen extends from the distal end of the ligating device to a proximal end thereof and wherein the ligating band dispenser is adapted to support a plurality of first ligating bands, the ligating band dispenser comprising:
   a support structure for attachment to the distal end of the ligating device, wherein the first ligating bands are received around an outer surface of the support structure and wherein a passage extends through the support structure to communicate with the lumen; and
   a first displacement element looped about each of the first ligating bands in series, the first displacement element extending through the passage to a distal end of the lumen, whereby proximal motion of the first displacement element from the proximal end of the ligating device transfers a distal-most one of the first ligating bands off a distal end of the support structure;
   wherein the support structure includes a plurality of notches and, wherein the first displacement element extends through a first one of the notches, over, around and under a first one of the first ligating bands and returns to a returned-to-notch selected from one of the first notch and a corresponding second notch; and
   wherein for all but a proximal-most one of the first ligating bands, the first displacement element extends from the returned-to-notch to a second one of the notches and then under, around and over a second one of the first ligating bands.

4. A ligating band dispenser adapted to support a plurality of first ligating bands, the ligating band dispenser comprising:
   a support structure for attachment to a distal end of a ligating device, wherein the first ligating bands are received around an outer surface of the support structure and wherein a passage extends through the support structure to communicate with a lumen of the ligating device; and a displacement element extending through the passage to a distal edge of the support structure, wherein the displacement element wraps around the distal edge of the support structure to loop around a distal-most one of the first ligating bands, passes back to the distal edge of the support structure and then extends proximally along the outer surface of the support structure to loop around a second one of the first ligating bands.

5. The ligating band dispenser of claim 4 further comprising a second displacement element looped about each of the first ligating bands in series, wherein the second displacement element is looped about the first ligating bands at a location spaced from the first displacement element.

6. The ligating band dispenser of claim 4, in which the displacement element includes a stop for preventing movement of a distal end of the displacement element proximally past a predetermined position.

7. The ligating band dispenser of claim 4, further comprising an operator coupled to a proximal end of the first displacement element, wherein the operator extends through the lumen to a proximal end of the lumen.

8. The ligating band dispenser of claim 4, in which the first displacement element is looped about at least one of the first ligating bands so that slack is provided in the loop.

9. The ligating band dispenser of claim 4, in which the support structure includes a tubular body having a substantially cylindrical exterior surface for carrying the ligating bands, and wherein the tubular body has a proximal shoulder portion and a connector for connecting the shoulder portion to the distal end of the ligating device.

10. The ligating band dispenser of claim 4, wherein at least one second ligating band is received on the support structure, the ligating band dispenser further comprising a second displacement element, wherein the second displacement element is looped about the at least one second ligating band.

* * * * *